(12) United States Patent
Michalak et al.

(10) Patent No.: US 9,070,553 B2
(45) Date of Patent: Jun. 30, 2015

(54) CYCLIC CARBOSILANE DIELECTRIC FILMS

(71) Applicant: Intel Corporation, Santa Clara, CA (US)

(72) Inventors: David J. Michalak, Portland, OR (US); James M. Blackwell, Portand, OR (US); James S. Clarke, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 13/894,422

(22) Filed: May 14, 2013

(65) Prior Publication Data
US 2013/0249049 A1 Sep. 26, 2013

Related U.S. Application Data

(62) Division of application No. 12/978,385, filed on Dec. 23, 2010, now Pat. No. 8,441,006.

(51) Int. Cl.
H01L 51/00 (2006.01)
H01L 21/02 (2006.01)
C07F 7/08 (2006.01)
C07F 7/18 (2006.01)
C09D 183/14 (2006.01)
H01L 29/06 (2006.01)

(52) U.S. Cl.
CPC ...... *H01L 21/02203* (2013.01); *H01L 51/0035* (2013.01); *H01L 51/0094* (2013.01); *H01L 21/02126* (2013.01); *H01L 21/02216* (2013.01); *H01L 21/02282* (2013.01); *C07F 7/0816* (2013.01); *C07F 7/1844* (2013.01); *C09D 183/14* (2013.01); *H01L 29/0649* (2013.01)

(58) Field of Classification Search
CPC ............ H01L 21/02203; H01L 21/02216; H01L 51/0035; H01L 51/0094
USPC ............ 257/40, E51.001, E51.024, E51.027; 438/99, 623, 780
See application file for complete search history.

(56) References Cited

U.S. PATENT DOCUMENTS

| 7,071,091 B2 | 7/2006 | Clarke et al. |
| 7,479,306 B2 | 1/2009 | Edelstein et al. |
| 7,497,965 B2 | 3/2009 | Wariishi et al. |
| 7,595,555 B2 | 9/2009 | Clarke et al. |
| 7,888,220 B2 | 2/2011 | Rachmady et al. |

(Continued)

FOREIGN PATENT DOCUMENTS

WO 2012/087750 A1 6/2012

OTHER PUBLICATIONS

Landskron et al., "Periodic Mesoporous Organosilicas Containing Interconnected [Si(CH2)]3 Rings." Science, 302, 266 (2003): pp. 266-269.*

(Continued)

*Primary Examiner* — Michele Fan
(74) *Attorney, Agent, or Firm* — Julia A Hodge

(57) ABSTRACT

Embodiments of the invention provide dielectric films and low-k dielectric films and methods for making dielectric and low-k dielectric films. Dielectric films are made from carbosilane-containing precursors. In embodiments of the invention, dielectric film precursors comprise attached porogen molecules. In further embodiments, dielectric films have nanometer-dimensioned pores.

7 Claims, 10 Drawing Sheets

(56) References Cited

U.S. PATENT DOCUMENTS

| | | | |
|---|---|---|---|
| 7,947,799 | B2 | 5/2011 | Landskron et al. |
| 2004/0137241 | A1 | 7/2004 | Lin et al. |
| 2006/0078676 | A1* | 4/2006 | Lukas et al. ............... 427/248.1 |
| 2006/0165891 | A1* | 7/2006 | Edelstein et al. .......... 427/248.1 |
| 2006/0172531 | A1* | 8/2006 | Lin et al. ........................ 438/637 |
| 2007/0173401 | A1 | 7/2007 | Landskron et al. |
| 2008/0009141 | A1 | 1/2008 | Dubois et al. |
| 2008/0150091 | A1 | 6/2008 | Lin |
| 2008/0223287 | A1 | 9/2008 | Lavoie et al. |
| 2008/0268177 | A1* | 10/2008 | Vrtis et al. .................... 427/585 |
| 2008/0271640 | A1* | 11/2008 | Vrtis et al. ............... 106/287.11 |
| 2009/0130412 | A1 | 5/2009 | Hatton et al. |
| 2010/0200991 | A1 | 8/2010 | Rohan et al. |
| 2011/0079862 | A1 | 4/2011 | Rachmady et al. |

OTHER PUBLICATIONS

Office Action Received for Taiwanese Patent Application No. 100147132, mailed on Dec. 24, 2013, 5 Pages of Taiwanese Office Action and 5 Pages of English Translation.

Baklanov et al., "Dielectric Films for Advanced Microelectronics," West Sussex, England: John Wiley & Sons Ltd, 2007, pp. 33-83.

Hoffmann et al., "Silica-Based Mesoporous Organic-Inorganic Hybrid Materials," Angewandte Chemie, 2006, pp. 3216-3251.

International Search Report and Written Opinion received for PCT Patent Application No. PCT/US2011/065196, mailed on Jun. 1, 2012, 11 pages.

Landskron et al., "Periodic Mesoporous Organosilicas: Self-Assembly from Bridged Cyclic Silsesquioxane Precursors," Angewandte Chem, vol. 44, Issue 14, Mar. 29, 2005, pp. 2107-2109.

Wang et al., "Water Repellent Periodic Mesoporous Organosilicas," ACS Nano, vol. 5, 2011, pp. 1267-1275.

Wang et al., "Vacuum-Assisted Aerosol Deposition of a Low-Dielectric-Constant Periodic Mesoporous Organosilica Film," Advance Materials, vol. 22, Jan. 5, 2010, pp. 99-102.

Landskron et al., "Periodic Mesoporous Organosilicas Containing Interconnected [Si(CH2)]3 Rings," Science, vol. 302, Oct. 10, 2003, pp. 266-269.

International Preliminary Report on Patentability received for PCT Patent Application No. PCT/US2011/065196, mailed on Jul. 4, 2013, 7 pages.

* cited by examiner

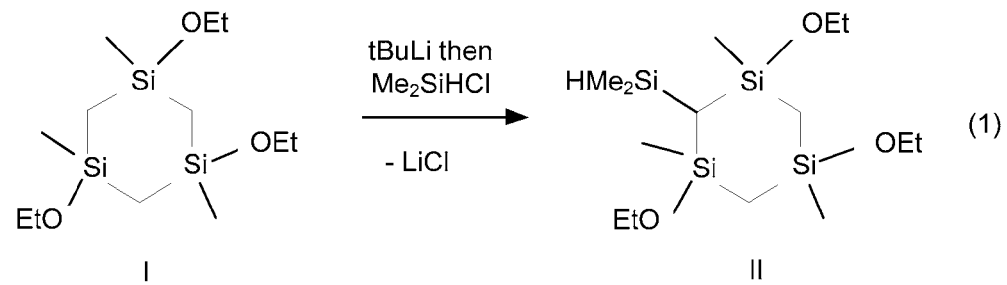
(1)
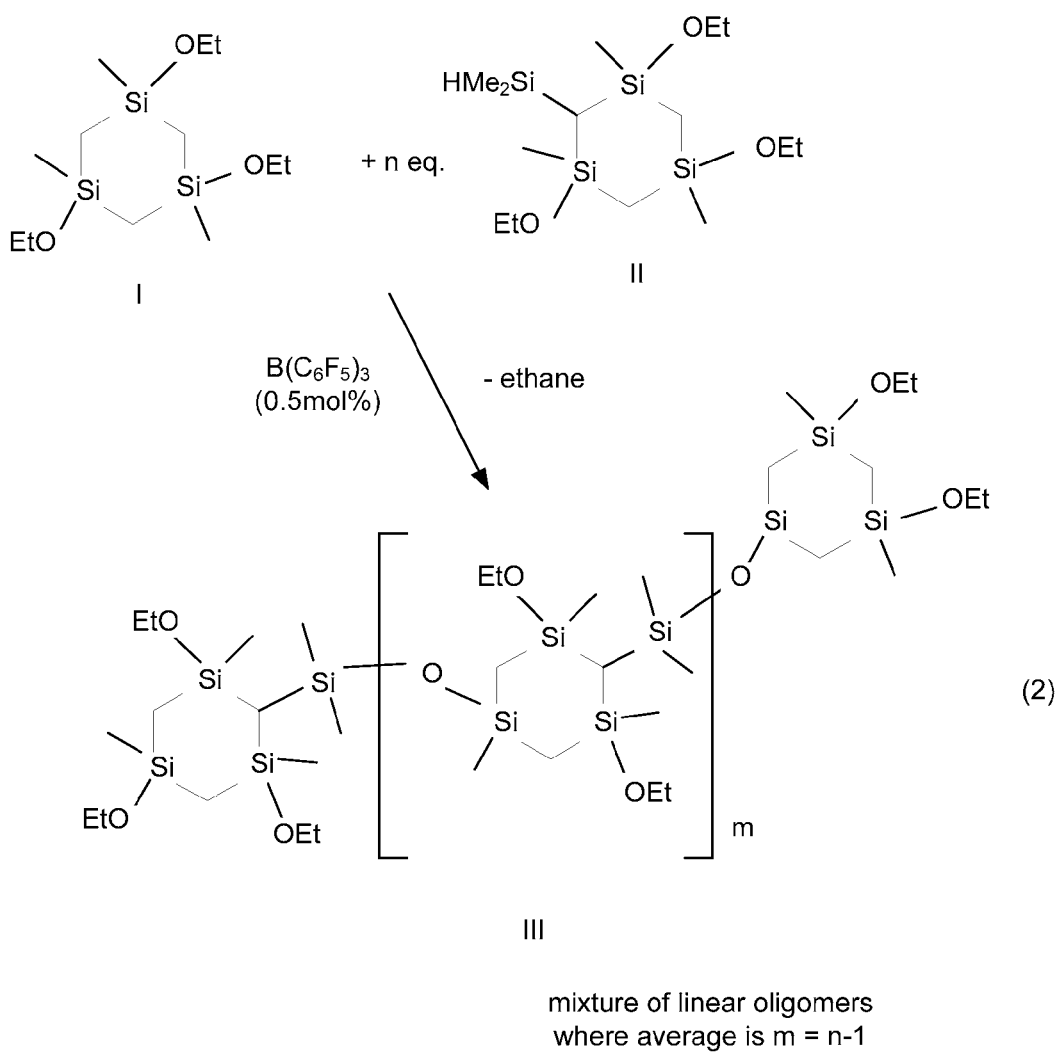
(2)
mixture of linear oligomers
where average is m = n-1
FIGURE 2

A
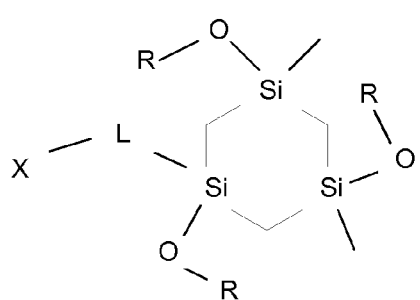
B
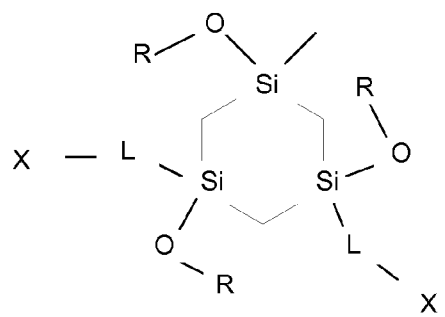
C
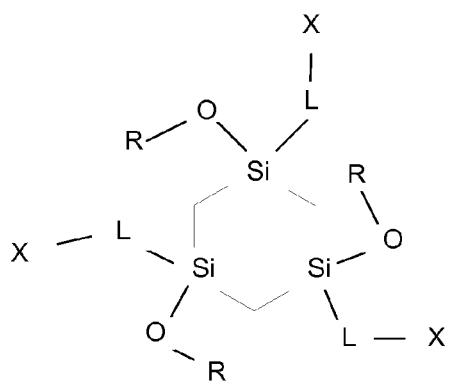
FIGURES 5A-C

A
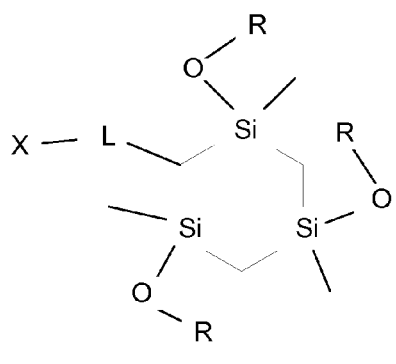
B
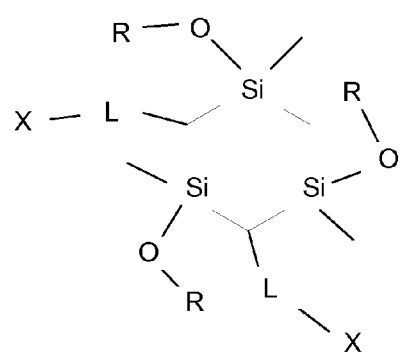
C
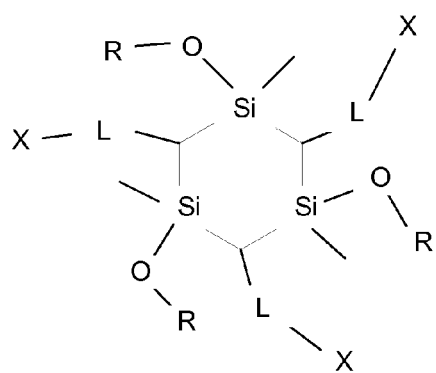
FIGURES 6A-C

CYCLIC CARBOSILANE DIELECTRIC FILMS

CROSS-REFERENCE TO RELATED APPLICATIONS

The present application is a Divisional application of U.S. Pat. No. 8,441,006 entitled "Cyclic Carbosilane Dielectric Films," filed Dec. 23, 2010, the disclosure of which is incorporated herein by reference.

BACKGROUND OF THE INVENTION

1. Field of the Invention

The embodiments of the invention relate generally to semiconductor processing and manufacture, integrated circuits, dielectric materials, interlayer dielectric materials, spin-on dielectric materials, and materials comprising cyclic carbosilanes.

2. Background Information

The desire for ever-smaller integrated circuits (IC) devices places enormous performance demands on the techniques and materials used to construct IC devices. In general, an integrated circuit chip is also known as a microchip, a silicon chip, or a chip. IC chips are found in a variety of common devices, such as the microprocessors in computers, cars, televisions, CD players, and cellular phones. A plurality of IC chips are typically built on a silicon wafer (a thin silicon disk, having a diameter, for example, of 300 mm) and after processing the wafer is diced apart to create individual chips. A 1 $cm^2$ IC chip having feature sizes around of about 90 nm can comprise hundreds of millions of components. Current technologies are pushing feature sizes even smaller than 45 nm.

BRIEF DESCRIPTION OF THE FIGURES

FIG. 2 illustrates a method for the synthesis of cyclic carbosilane precursors useful for making dielectric films and low-k dielectric films.

FIGS. 5A-C illustrate cyclic carbosilane precursor molecules useful for making dielectric films and low-k dielectric films.

FIGS. 6A-C show additional cyclic carbosilane precursor molecules useful for making dielectric films and low-k dielectric films.

DETAILED DESCRIPTION OF THE INVENTION

Embodiments of the invention provide dielectric films for integrated circuits. Cyclic carbosilane precursors are capable of providing films with small dielectric constants and the cyclic carbosilane precursors are useful in semiconductor processing applications. Dielectric films according to embodiments of the invention are useful in a variety of applications for integrated circuit devices. For example, the films described herein are useful as dielectric films, and low-k dielectric films, spin-on dielectric films, interlayer dielectric films (ILDs, intermetal dielectric films, or IMDs), and etch-selective layers.

Figure 1:
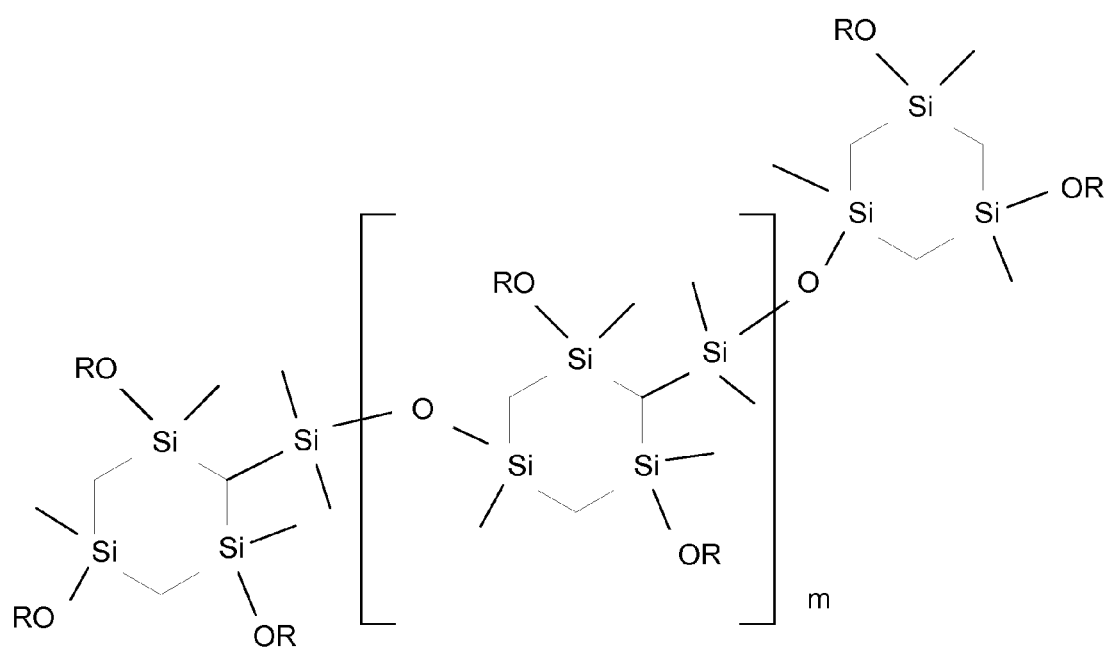
FIG. 1 shows cyclic carbosilane precursors useful for making dielectric films and low-k dielectric films.

FIG. 1 illustrates linear oligomers of cyclic carbosilane molecules that are useful as precursors for making dielectric films and low-k dielectric films. In FIG. 1, R is a functional group, such as, for example, an alkyl group comprising hydrogen atoms and from 1 to 10 carbon atoms or from 1 to a large number of carbon atoms. In addition, R also optionally comprises, oxygen atoms, nitrogen atoms, sulfur atoms, chlorine atoms, and or fluorine atoms. The functional group R is a group such as, for example, $-CH_3$, $-CH_2CH_3$, $-CH_2CH_2CH_3$, $-CH_2CH_2CH_2CH_3$, $-CH_2CH_2CH_2CH_2CH_3$, $-CH_2CH(CH_3)_2$, $-CH_2CH_2CH(CH_3)_2$, $-CH_2CH_2CH(CH_2CH_3)_2$, $-CH_2OCH_3$, $-CH_2CH_2OCH_3$, and others. In embodiments of the invention, the R group is less than 50% larger than the size of the porogen molecule chosen. In FIG. 1, m is a number from 1 to 10. In embodiments of the invention m is a number from 3 to 10. Other values for m are also possible, such as larger numbers. Further, one or two of the carbon atoms (i.e., $-CH_2-$ groups) in the cyclic carbosilane molecules is optionally replaced with an oxygen atom. The carbosilane oligomer composition that is used to create a dielectric film is typically a mixture of different oligomers having different lengths (different numbers of cyclic carbosilane units), so that m represents an average oligomer length for the molecules present in the mixture.

FIG. 2 provides a synthesis scheme for oligomers of cyclic carbosilane molecules that are useful as precursors for making dielectric films and low-k dielectric films. The cyclic carbosilane monomer is functionalized with crosslinking groups and then crosslinked with carbosilane monomers. Although, in FIG. 2, ethyl (-Et) functional groups are shown, other alkyl groups are also possible, such as, for example, an alkyl group comprising hydrogen atoms and from 1 to 10 carbon atoms or from 1 to a large number of carbon atoms. In addition, R also optionally comprises, oxygen atoms, nitrogen atoms, sulfur atoms, chlorine atoms, and or fluorine atoms. The functional group R is a group such as, for example, $-CH_3$, $-CH_2CH_3$, $-CH_2CH_2CH_3$, $-CH_2CH_2CH_2CH_3$, $-CH_2CH_2CH_2CH_2CH_3$, $-CH_2CH(CH_3)_2$, $-CH_2CH_2CH(CH_3)_2$, $-CH_2CH_2CH(CH_2CH_3)_2$, $-CH_2OCH_3$, $-CH_2CH_2OCH_3$, and others. In embodiments of the invention, the R group is less than 50% larger than the size of the porogen molecule chosen. Further, one or two of the carbon atoms of the cyclic carbosilanes is optionally replaced with an oxygen atom. In FIG. 2, scheme (1), molecule I (in this case, 1,3,5-triethoxy-1,3,5-trimethyl-1,3,5-trisilacyclohexane) is reacted with t-butyl lithium and then subsequently $Me_2SiHCl$ to form molecule II, in which one of the cyclic carbosilane ring carbons has been silanated. Molecule II is then reacted with molecule I in the presence of $B(C_8F_5)_3$ to yield a mixture of oligomers in which m is a function of the number of equivalents of molecule II used, such that m=n−1. The cyclic carbosilane oligomer composition produced by the method of FIG. 2 is often a mixture of different oligomers having different lengths, so that m represents an average oligomer length for the molecules present in the mixture.

Figure 3:
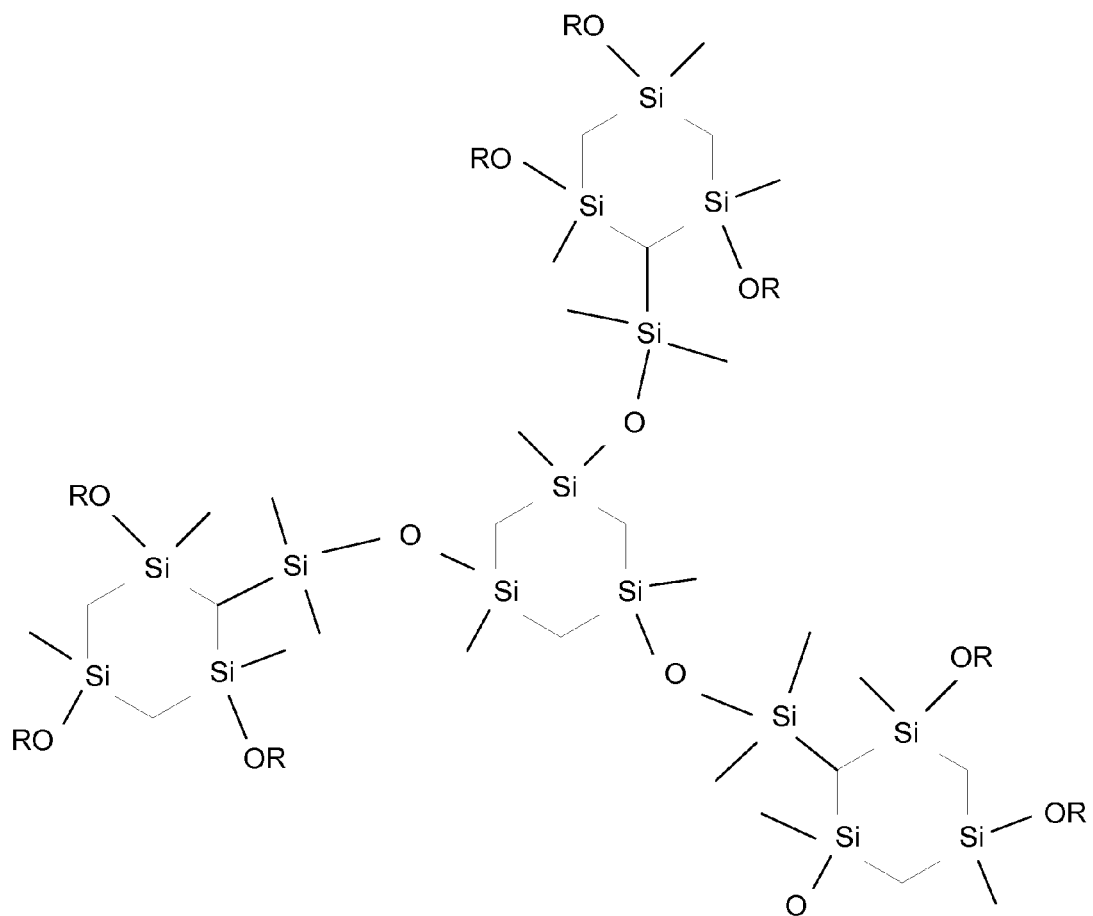
FIG. 3 shows an additional cyclic carbosilane precursor useful for making dielectric films and low-k dielectric films.

FIG. 3 provides an additional oligomeric cyclic carbosilane precursor useful for making dielectric and low-k dielectric films. The molecule of FIG. 3 is a branched oligomer. In FIG. 3, R is a functional group, such as, for example, an alkyl group comprising hydrogen atoms and from 1 to 10 carbon atoms or from 1 to a large number of carbon atoms. In addition, R also optionally comprises, oxygen atoms, nitrogen atoms, sulfur atoms, chlorine atoms, and fluorine atoms. The functional group R is a group such as, for example, —$CH_3$, —$CH_2CH_3$, —$CH_2CH_2CH_3$, —$CH_2CH_2CH_2CH_3$, —$CH_2CH_2CH_2CH_2CH_3$, —$CH_2CH(CH_3)_2$, —$CH_2CH_2CH(CH_3)_2$, —$CH_2CH_2CH(CH_2CH_3)_2$, —$CH_2OCH_3$, —$CH_2CH_2OCH_3$, and others. In embodiments of the invention, the R group is less than 50% larger than the size of the porogen molecule chosen. Further, one or two of the carbon atoms of the cyclic carbosilanes is optionally replaced with an oxygen atom. In additional embodiments, there are, for example, 1, 2, or 3 modified cyclic carbosilane groups around the central cyclic carbosilane group. Different oligomers comprising different numbers of cyclic carbosilane groups are possible.

Figure 4:
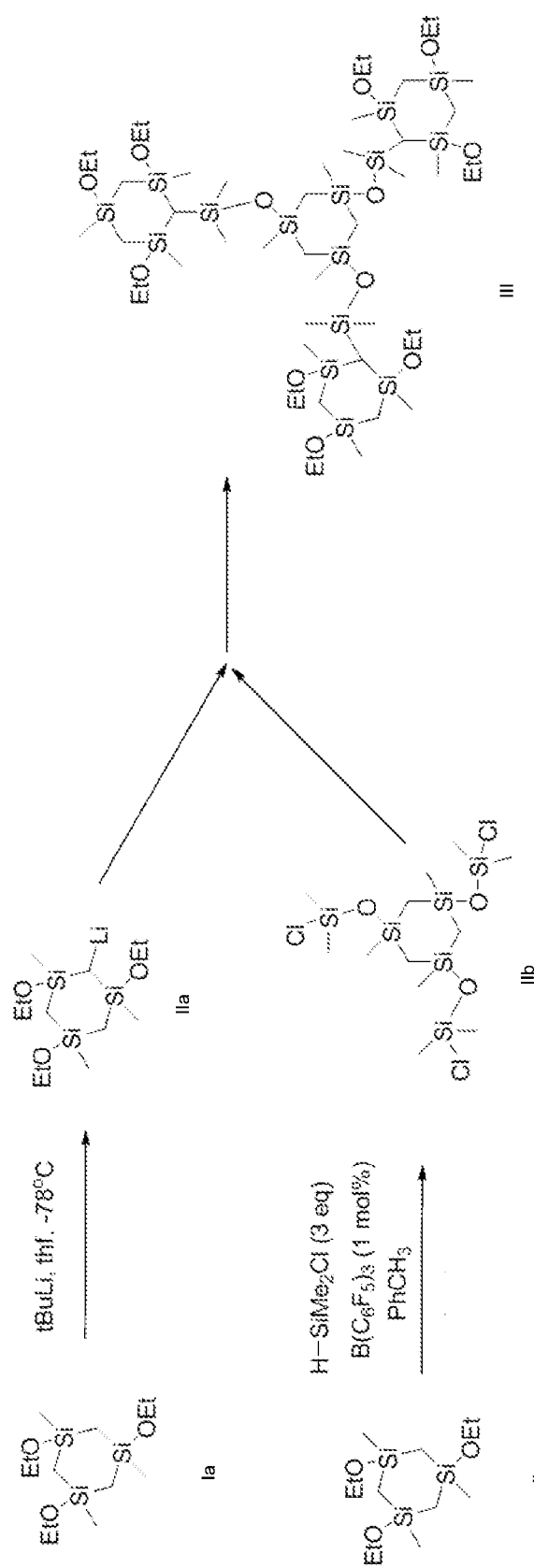
FIG. 4 illustrates a method for the synthesis of additional cyclic carbosilane precursors useful for making dielectric films and low-k dielectric films.

FIG. 4 illustrates methods for synthesizing a branched oligomeric cyclic carbosilane precursor. Although, in FIG. 4, ethyl (-Et) functional groups are shown, other alkyl groups are also possible, such as, for example, an alkyl group comprising hydrogen atoms, and from 1 to 10 carbon atoms or from 1 to a large number of carbon atoms. In addition, R also optionally comprises, oxygen atoms, nitrogen atoms, sulfur atoms, chlorine atoms, and or fluorine atoms. The functional group R is a group such as, for example, —$CH_3$, —$CH_2CH_3$, —$CH_2CH_2CH_3$, —$CH_2CH_2CH_2CH_3$, —$CH_2CH_2CH_2CH_2CH_3$, —$CH_2CH(CH_3)_2$, —$CH_2CH_2CH(CH_3)_2$, —$CH_2CH_2CH(CH_2CH_3)_2$, —$CH_2OCH_3$, —$CH_2CH_2OCH_3$, and others. In embodiments of the invention, the R group is less than 50% larger than the size of the porogen molecule chosen. Further, one or two of the carbon atoms of the cyclic carbosilanes is optionally replaced with an oxygen atom. In FIG. 4, two different methods of dendrimeric cyclic carbosilane precursor synthesis are shown. In FIG. 4, molecule Ia is reacted with t-butyl lithium to form molecule IIa. Molecule Ib is reacted with three equivalents of IIa to condense the molecules into molecule III. Alternately, in FIG. 4, molecule Ib is reacted with three equivalents of molecule IIb in the presence of $SiMe_2HCl$ and $B(C_6F_5)_3$ in toluene to make molecule III.

FIGS. 5A-C provide additional useful dielectric film precursor molecules that have attached porogens (pore-creating functional groups). In FIG. 5A, a cyclic carbosilane ring comprises a porogen functional group, X, linked to a silicon of the carbosilane ring through a linker group, L. In FIG. 5B the cyclic carbosilane ring comprises two porogen functional groups, X, linked to silicon atoms of the carbosilane ring through a linker group, L. In FIG. 5C the cyclic carbosilane ring comprises three porogen functional groups, X, linked to silicon atoms of the carbosilane ring through a linker group, L. In alternate embodiments, one or two of the carbon atoms (i.e., —$CH_2$— groups) of the cyclic carbosilane ring is replaced with an oxygen atom. In an embodiment of the invention, porogen functional groups have dimensions (widths, lengths, and heights or radii) that are from 0.25 nm to 2 nm. In alternate embodiments, the porogen functional groups have dimensions that are from 0.25 nm to 0.5 nm or from 0.5 nm to 5 nm. Pore sizes in the resulting films have dimensions (widths, lengths, and heights or radii, depending on the shape of the pore) that are from 0.25 nm to 2 nm (or from 0.25 nm to 0.5 nm or from 0.5 nm to 5 nm), depending on the porogen group chosen. Further, porogen groups decompose (upon heating, UV curing, or electron beam curing, for example) with approximately 100% volatile yield (approximately indicating 80%±20%). Porogen functional groups are, for example, cyclodextrins, polyethylene oxides, polystyrenes, polyacrylates, or poly-alpha-methylstyrenes. Linker groups are carbon-containing groups containing hydrogen and carbon atoms. Linker groups also optionally contain oxygen atoms. Linkers include groups, such as for example, —$CH_2$—, —$OCH_2$—, —$CH_2O$—, —$CH_2CH_2$—, —$CH_2OCH_2$—, —$CH_2(CH_3)CH_2$—. The functional group labeled R in FIGS. 5A-C is an alkyl group comprising hydrogen atoms and from 1 to 10 carbon atoms or from 1 to a large number of carbon atoms. In addition, R also optionally comprises, oxygen atoms, nitrogen atoms, sulfur atoms, chlorine atoms, and or fluorine atoms. The functional group R is a group such as, for example, —$CH_3$, —$CH_2CH_3$, —$CH_2CH_2CH_3$, —$CH_2CH_2CH_2CH_3$, —$CH_2CH_2CH_2CH_2CH_3$, —$CH_2CH(CH_3)_2$, —$CH_2CH_2CH(CH_3)_2$, —$CH_2CH_2CH(CH_2CH_3)_2$, —$CH_2OCH_3$, —$CH_2CH_2OCH_3$, and others. In embodiments of the invention, the R group is less than 50% larger than the size of the porogen molecule chosen.

FIGS. 6A-C provide further additional useful dielectric film precursor molecules that have attached porogens (pore-creating functional groups). In FIG. 6A, a cyclic carbosilane ring comprises a porogen functional group, X, linked to a carbon of the carbosilane ring through a linker group, L. In alternate embodiments of the invention, one or two of the carbon atoms (—$CH_2$— groups) of the cyclic carbosilane ring is replaced with an oxygen atom. In FIG. 6B the cyclic carbosilane ring comprises two porogen functional groups, X, linked to carbon atoms of the carbosilane ring through a linker group, L. In alternate embodiments of the invention, one of the carbon atoms (—$CH_2$— groups) of the cyclic carbosilane ring is replaced with an oxygen atom. In FIG. 6C the cyclic carbosilane ring comprises three porogen functional groups, X, linked to carbon atoms of the carbosilane ring through a linker group, L. In an embodiment of the invention, porogen functional groups have dimensions (widths, lengths, and heights or radii) that are from 0.25 nm to 2 nm. In alternate embodiments, the porogen functional groups have dimensions that are from 0.25 nm to 0.5 nm or from 0.5 nm to 5 nm. Pore sizes in the resulting films have dimensions (widths, lengths, and heights or radii, depending on the shape of the pore) that are from 0.25 nm to 2 nm (or from 0.25 nm to 0.5 nm or from 0.5 nm to 5 nm), depending on the porogen group chosen. Further, porogen groups decompose (upon heating, UV curing, or electron beam curing, for example) with approximately 100% volatile yield (approximately indicating 80%±20%). Porogen functional groups are, for example, cyclodextrins, polyethylene oxides, polystyrenes, polyacrylates, or poly-alpha-methylstyrenes. Linker groups are carbon-containing groups containing hydrogen and carbon atoms. Linker groups also optionally contain oxygen atoms. Linkers include groups, such as for example, —$CH_2$—, —$OCH_2$—, —$CH_2O$—, —$CH_2CH_2$—, —$CH_2OCH_2$—, —$CH_2(CH_3)CH_2$—. The functional group labeled R in FIGS. 5A-C is an alkyl group comprising hydrogen atoms and from 1 to 10 carbon atoms or from 1 to a large number of carbon atoms. In addition, R also optionally comprises, oxygen atoms, nitrogen atoms, sulfur atoms, chlorine atoms, and or fluorine atoms. The functional group R is a group such as, for example, —$CH_3$, —$CH_2CH_3$, —$CH_2CH_2CH_3$, —$CH_2CH_2CH_2CH_3$, —$CH_2CH_2CH_2CH_2CH_3$, —$CH_2CH(CH_3)_2$, —$CH_2CH_2CH(CH_3)_2$, —$CH_2CH_2CH(CH_2CH_3)_2$, —$CH_2OCH_3$, —$CH_2CH_2OCH_3$, and others. In embodiments of the invention, the R group is less than 50% larger than the size of the porogen molecule chosen.

Figure 7:
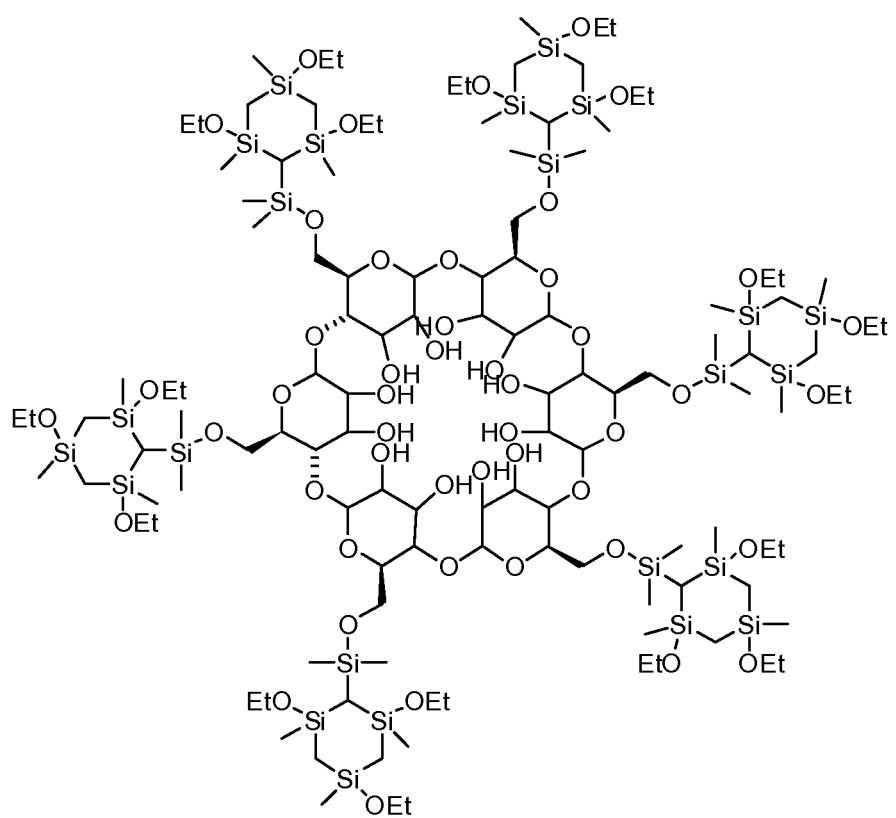
FIG. 7 provides a cyclic carbosilane-attached porogen molecule.

FIG. 7 provides a porogen molecule linked to a plurality of carbosilane rings. In FIG. 7, the porogen molecule is an alpha cyclodextrin molecule comprises six attached cyclic carbosilanes. Each cyclic carbosilane is attached to one porogen molecule in this embodiment. The carbosilane-linked porogen molecule of FIG. 7 can be made, for example, by reacting the cyclodextrin with about 6 equivalents of molecule II of FIG. 2 in the presence of $B(C_6F_5)_3$ in toluene.

Figure 8:
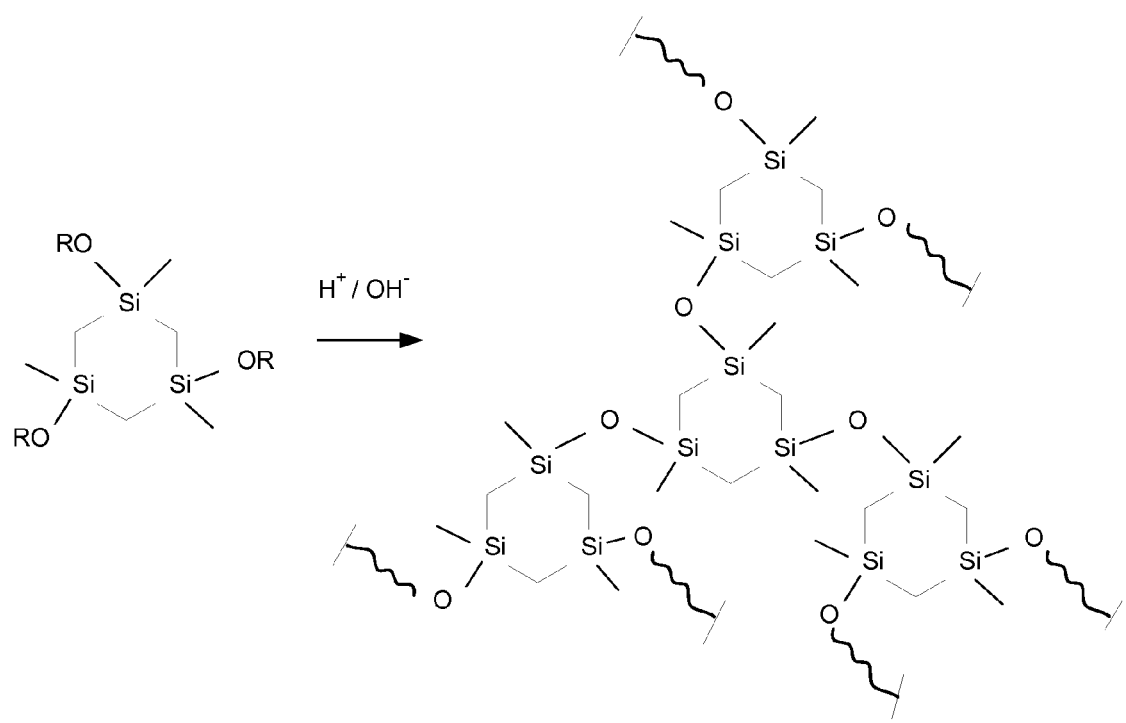
FIG. 8 shows the acid or base catalyzed polymerization of cyclic carbosilane molecules.

FIG. 8 illustrates generally the acid or base catalyzed crosslinking of an exemplary cyclic carbosilane molecule. Through acid or base catalyzed reactions similar to the one illustrated in FIG. 8, liquid-phase carbosilane film precursors of FIGS. 1-7 become solidified films. In FIG. 8, R is an alkyl functional group such as one described with respect to any one of FIGS. 1-6.

Figure 9:
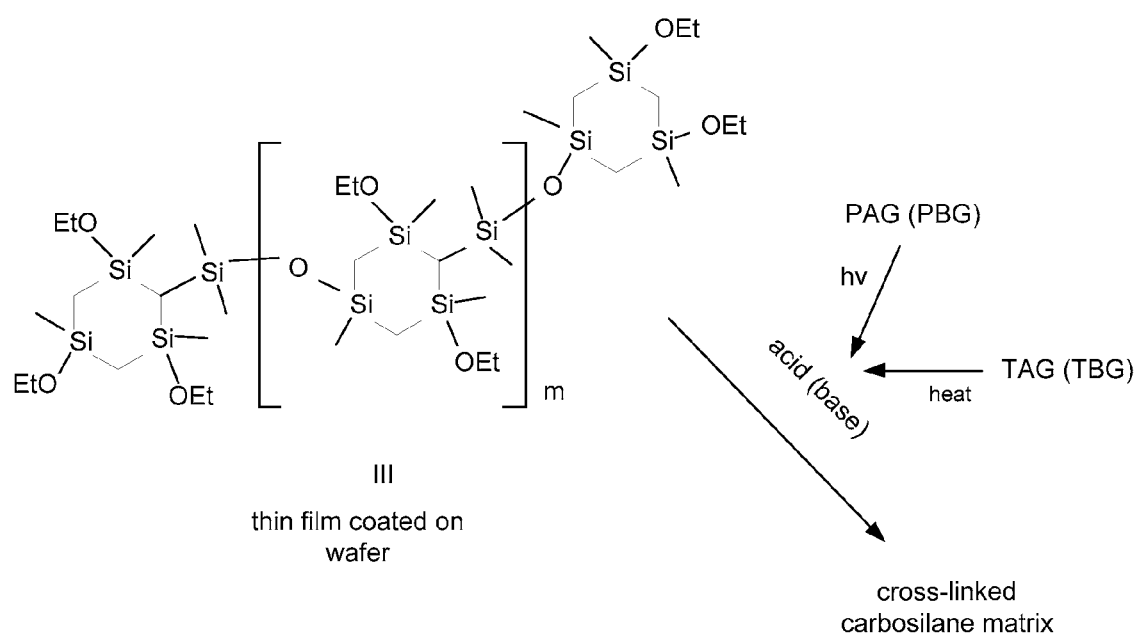
FIG. 9 illustrates a synthesis scheme for making dielectric films and low-k dielectric films.

FIG. 9 shows the formation of a dielectric film on a substrate. In FIG. 9, a cyclic carbosilane precursor that is an oligomer of cyclic carbosilane units (molecule III in FIG. 9), is mixed with a photo acid generator (PAG), a photo base generator (PGB), a thermally-activated acid generator (TAG) or a thermally-activated base generator (TBG), spun onto a substrate surface, such as a semiconductor wafer surface, and exposed to either heat or light to activate the acid- or base-producing compound. A photo acid generator or photo base generator is exposed to light to produce an acid or a base (respectively) and a thermally-activated acid or a thermally-activated base is exposed to heat to produce an acid or a base (respectively). Once the acid or base species is produced, crosslinking of the carbosilane precursors occurs and the film solidifies. In this manner a dielectric and or a low-k dielectric film is produced. Cyclic carbosilane precursors according to FIGS. 1, 3, 5A-C, 6A-C, and 7 and mixtures thereof are useful for forming dielectric films in the method described in FIG. 9. Mixtures of porogen-comprising precursors and non-porogen containing precursors are used to generate films having desired porosities.

In general, exemplary photo acid generators are diaryliodonium and triarylsulfonium salts possessing weakly coordinating counter anions such as trifluoromethanesulfonate, nonafluororbutanesulfonate, hexafluorophosphate, tetrafluoroborate, para-toluenesulfonate, and others. Examples of neutral photoacid generators include those in the arylsulfonate family such as phenyltrifluoromethanesulfonate and those in the N-sulfonated amine and imides family such as N-trifluoromethanesulfonatomaleimide. Other classes of compounds common in the photolithographic and photopolymerization fields are also useful in embodiments of the invention. Examples of photobase generators include amines protected with photodecomposable nitrobenzylcarbamate or other carbamate groups. Other classes of compounds common in the photolithographic and photopolymerization fields and used as PAGs and PBGs are also useful in embodiments of the invention. Through the introduction of less stable substituents, the above described photoacid and photobase generators can be tuned to also behave as thermal acid and thermal base generators, respectively. For example, sulfonium salts possessing two aryl substituents and one alkyl substituent can behave as thermal acid generators. Additionally, due to the thermal instability of carbamate towards the release of $CO_2$, common photobase generators can also serve as thermal base generators in films. Typical temperatures for carbamate-containing TAGs are temperatures between 200 and 400° C. Although, other photo and thermally-activated acid and photo and thermally-activated base generators are possible.

Figure 10:
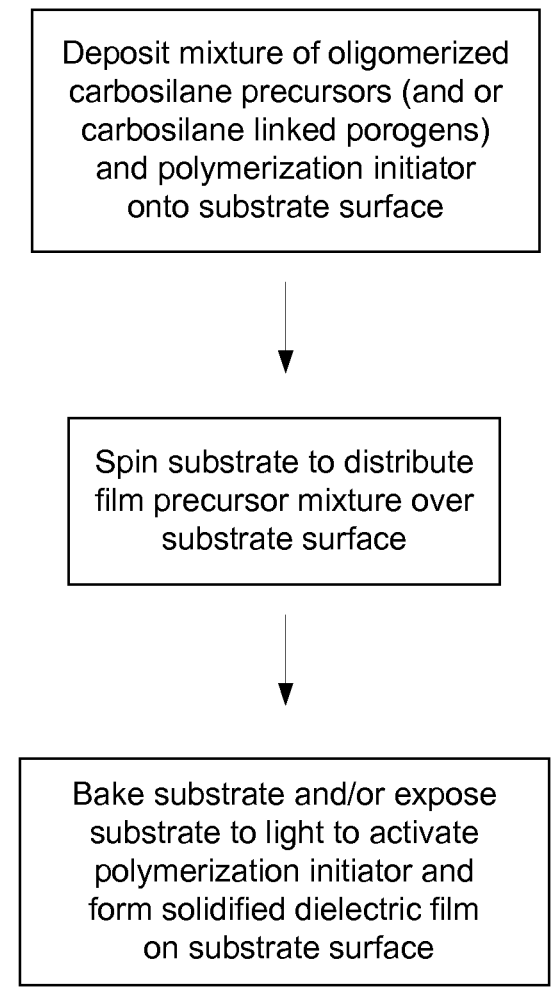
FIG. 10 describes a method for making a dielectric films and low-k dielectric films.

FIG. 10 describes a method for the formation of a spin-on-dielectric film. In FIG. 10, a mixture of a polymerization initiator and oligomerized carbosilane precursors is deposited onto a substrate surface. In an alternate embodiment the mixture of the polymerization initiator and the oligomerized carbosilane precursors additionally comprises porogen-linked cyclic carbosilanes. In further embodiments the mixture comprises a polymerization initiator and porogen-linked cyclic carbosilanes. In embodiments of the invention, oligomers comprise between 3 and 10 cyclic carbosilane units. The polymerization initiator is a photo acid generator, a photo base generator, a thermally-activated acid, or a thermally-activated base. The substrate is spun distributing the film precursor mixture across the substrate surface. The polymerization initiator is then activated through exposing the substrate surface to light for photo-activated initiators or heating the substrate surface for heat-activated initiators. Polymerization of the cyclic carbosilanes creates a solidified film.

Depending on the composition of the film precursors used, the resulting film has a porosity that is between 5% and 60%. In additional embodiments the resulting film has a porosity that is between 25% and 60%, between 35% and 50%, or between 35% and 45%. In general, porosity is a measure of the space taken up by empty space (pores) in the material, and is described as a fraction of the volume of the empty space over the total volume of the material. The pores in the resulting films have dimensions that are that are from 0.25 nm to 2 nm. In alternate embodiments, the pores have dimensions that are from 0.25 nm to 0.5 nm or from 0.5 nm to 5 nm Additionally, the resulting films are hydrophobic. As used herein, hydrophobic means that the films do not absorb or adsorb significant amounts of water from the atmosphere. In embodiments of the invention, less than 5% water uptake (as a volume of water taken up by the film to total volume of the film) is observed for the hydrophobic carbosilane films as measured by ellipsometric porosimetry in a saturated $H_2O$ atmosphere at room temperature (20 to 23.5° C.). In additional embodiments, less than 3% water uptake or less than 1% water uptake is observed for the hydrophobic carbosilane films as measured by ellipsometric porosimetry.

The dielectric constant (k) values for the carbosilane films range from 1.6 to 3.5. In additional embodiments, the dielectric constant (k) values for the carbosilane films are from 1.6 to 3.0, or from 1.6 to 2.5. Dielectric constant values are measured using a CV dot technique in which the film is deposited on a highly doped Si substrate and metallic dots are deposited on top of the film. The dielectric constant across the film is then measured.

Additionally, films according to embodiments of the invention have percent compositions in the range of 45-60% C, 25-35% Si, and 10-20% 0 (atomic percent).

Films according to embodiments of the invention are chemically stable. In general, chemical stability means that the film is significantly resistant to chemical degradation. For example, chemically stable films according to embodiments of the invention are resistant to degradation when a sample of the film is placed in a solution of 0.5% HF (at 23° C.), 1.0% KOH (at 50° C.), 15% TMAH (tetramethylammonium hydroxide) (at 60° C.), or 30% $H_2O_2$ (at 50° C.) for 10 minutes. Resistant to degradation means that 10 nm or less of film loss and 5% or less change in refractive index is observed.

In general, a porogen molecule or functional group is a molecule or functional group that is present in the precursor film that is capable of creating pores in the final film. Typically the porogen molecule is removed from the final film through heating, although other methods are possible. Other methods for porogen removal, include, for example, UV-curing or electron beam curing. After removal, the space occupied by the porogen molecule becomes a pore.

The substrate on which the devices that make up the IC circuit chip are built and dielectric films are used is, for example, a silicon wafer or a silicon-on-insulator substrate. Silicon wafers are substrates that are typically used in the semiconductor processing industry, although embodiments of the invention are not dependent on the type of substrate used. The substrate could also be comprised of, for example, germanium, indium antimonide, lead telluride, indium arsenide, indium phosphide, gallium arsenide, gallium antimonide, and or other Group III-V materials either alone or in combination with silicon or silicon dioxide or other insulating materials. IC devices that make up the chip are built on the substrate surface. Devices are optionally distributed across the substrate surface and or stacked on top of each other.

In general, a spin-on-dielectric film (SOD) is a dielectric film created by spinning a solution to distribute it across a surface and then solidifying the solution on the surface. A liquid form of the film is placed in the center of the substrate (such as a wafer). The substrate is spun causing the liquid film material to distribute across the wafer surface. The thickness of the resulting film depends in part on the viscosity of the liquid film. Excess liquid film material is spun off the substrate.

In general a low-k dielectric material is a dielectric material that has a lower dielectric constant that silicon dioxide ($SiO_2$). Silicon dioxide has a dielectric constant of 3.9. The use of low-k dielectric materials in integrated circuit devices has enabled continued device size reduction. Although a variety of materials have lower dielectric constants that $SiO_2$ not all materials are suitable for integration into integrated circuits and integrated circuit manufacturing processes.

An inter-layer dielectric (ILD) or inter-metal dielectric (IMD) film is the insulating material used between metal conductors and devices (such as transistors) in integrated circuit devices.

Persons skilled in the relevant art appreciate that modifications and variations are possible throughout the disclosure and combinations and substitutions for various components shown and described. Reference throughout this specification to "one embodiment" or "an embodiment" means that a particular feature, structure, material, or characteristic described in connection with the embodiment is included in at least one embodiment of the invention, but does not necessarily denote that they are present in every embodiment. Furthermore, the particular features, structures, materials, or characteristics may be combined in any suitable manner in one or more embodiments. Various additional layers and or structures may be included and or described features may be omitted in other embodiments.

We claim:

1. A device comprising,
   a substrate,
   a dielectric film disposed on the substrate, wherein the dielectric film is comprised of crosslinked cyclic carbosilanes wherein a cyclic carbosilane has a ring structure comprising carbon and silicon, wherein the dielectric film is porous and the porosity is in the range of 25% to 60%, and wherein the dielectric film comprises between 45 and 60 atomic percent C, between 25 and 35 atomic percent Si, and between 10 and 20 atomic percent O.

2. The device of claim 1 wherein the pores of the dielectric film have dimensions that are between 0.25 nm and 2 nm.

3. The device of claim 1 wherein the dielectric film has a k value of from 1.6 to 2.5.

4. The device of claim 1 wherein the dielectric film is porous and the porosity of the film is in the range of 35% and 50%.

5. The device of claim 1 wherein the substrate additionally comprises the components of an integrated circuit device and the dielectric film is between at least two components of the integrated circuit device.

6. The device of claim 1 wherein the film is chemically stable.

7. The device of claim 1 wherein the dielectric film additionally comprises a photo acid generator, a photo base generator, a thermally-activated acid generator, or a thermally-activated base generator.

* * * * *